(12) United States Patent
Niemann et al.

(10) Patent No.: US 9,255,919 B2
(45) Date of Patent: Feb. 9, 2016

(54) GAS SENSOR, IN PARTICULAR FOR AUTOMOBILE APPLICATIONS

(75) Inventors: Thomas Niemann, Delmenhorst (DE); Torsten Eggers, Bremen (DE)

(73) Assignee: Hella KGAA Hueck & Co., Lippstadt (DE)

( * ) Notice: Subject to any disclaimer, the term of this patent is extended or adjusted under 35 U.S.C. 154(b) by 231 days.

(21) Appl. No.: 14/002,725

(22) PCT Filed: Feb. 28, 2012

(86) PCT No.: PCT/DE2012/000186
§ 371 (c)(1),
(2), (4) Date: Sep. 26, 2013

(87) PCT Pub. No.: WO2012/116681
PCT Pub. Date: Sep. 7, 2012

(65) Prior Publication Data
US 2014/0007649 A1  Jan. 9, 2014

(30) Foreign Application Priority Data
Mar. 1, 2011  (DE) .......................... 10 2011 012 682

(51) Int. Cl.
*G01N 33/497* (2006.01)
*G01N 33/00* (2006.01)
*G01N 27/12* (2006.01)

(52) U.S. Cl.
CPC ............ *G01N 33/0009* (2013.01); *G01N 27/12* (2013.01)

(58) Field of Classification Search
CPC ............ G01N 33/0009; G01N 27/127; G01N 33/0004; G01N 27/4077; G01N 27/4078; B82Y 30/00; H01L 2924/0002; H01L 2924/00; H01L 33/60; F21Y 2101/02; B60R 2021/2648; Y02T 10/47; Y02T 90/32; H01M 2250/20; B60H 1/008
USPC ......................................................... 73/23.2
See application file for complete search history.

(56) References Cited

U.S. PATENT DOCUMENTS 5,659,127 A * 8/1997 Shie et al. .................... 73/31.05
5,689,059 A * 11/1997 Oh et al. ...................... 73/23.31

(Continued)

FOREIGN PATENT DOCUMENTS

CN          1258031 A    6/2000
CN          1295251 A    5/2001

(Continued)

*Primary Examiner* — Peter Macchiarolo
*Assistant Examiner* — Mohammed Keramet-Amircolai
(74) *Attorney, Agent, or Firm* — Muncy, Geissler, Olds & Lowe, P.C.

(57) ABSTRACT

For a gas sensor, in particular for automobile applications, comprising a housing, which has a measurement chamber, wherein at least one sensor element having connecting wires is associated with the measurement chamber, the housing has a bottom part and a top part that covers the bottom part and each sensor element is arranged in the bottom part while suspended by the connecting wires thereof. At least one side wall of the bottom part favorably has an assembly opening, which is designed in such a way that a tool arm that retains the sensor element can be inserted into the bottom part from the outside through the assembly opening and can be brought into an assembly position in the area of the opening edge of the bottom part so that the connecting wires of the sensor element are in bondable contact with the associated connection surfaces. Thus especially easy assembly is possible.

5 Claims, 1 Drawing Sheet

(56) References Cited

U.S. PATENT DOCUMENTS

| | | | |
|---|---|---|---|
| 6,565,812 B1 | 5/2003 | Nomura et al. | |
| 7,708,869 B2 * | 5/2010 | Yamada | 204/428 |
| 2006/0162423 A1 * | 7/2006 | Ruth | 73/23.31 |

FOREIGN PATENT DOCUMENTS

| CN | 101546209 A | 9/2009 |
|---|---|---|
| CN | 201770419 U | 3/2011 |
| CN | 102216097 A | 10/2011 |
| DE | 43 06 268 A1 | 9/1994 |
| DE | 195 34 918 A1 | 1/1997 |
| DE | 103 28 356 A1 | 1/2005 |
| DE | 10 2005 003 657 A1 | 2/2006 |
| DE | 20 2007 003 333 U1 | 7/2007 |
| EP | 0 764 847 A1 | 3/1997 |
| JP | 61-195339 A | 8/1986 |
| JP | 2008-14662 A | 1/2008 |
| WO | WO 2009/068405 A1 | 6/2009 |
| WO | WO 2010/057700 A1 | 5/2010 |

* cited by examiner

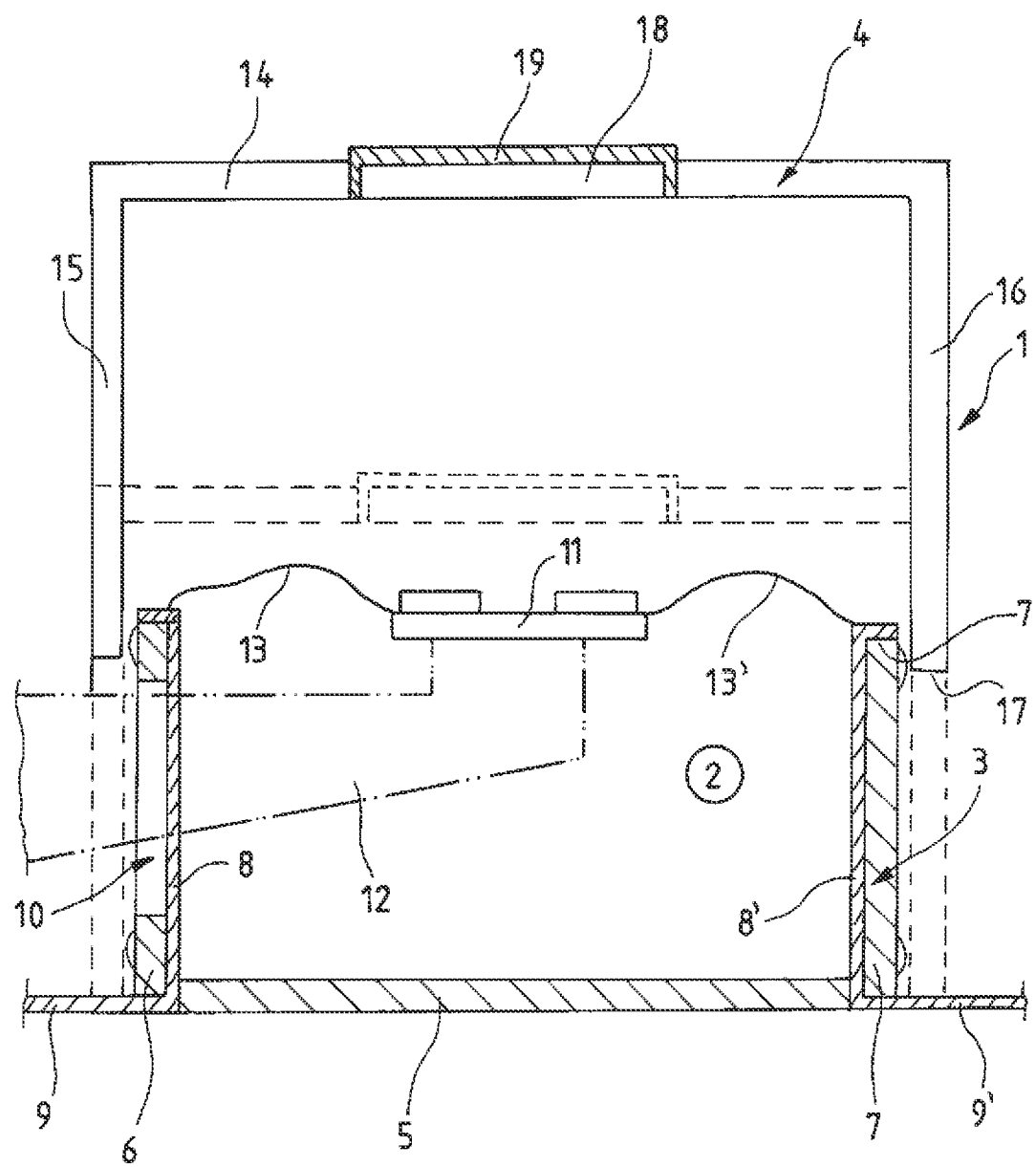

GAS SENSOR, IN PARTICULAR FOR AUTOMOBILE APPLICATIONS

The invention relates to a gas sensor, in particular a gas sensor for automobile applications, comprising a housing, which has a measurement chamber, which is assigned at least one sensor element having connecting wires.

DE 101 33 466 B4 provides a gas sensor which is integrated in a layered composite. A support element for a multifunctional sensor is described in DE 10 2008 034 03.

Gas sensors of the aforementioned genre are used inter alia in the field of vehicle ventilation in order to protect the occupants from adverse effects due to impurities of the supplied fresh air.

Known gas sensors, in particular their housing enclosing the measurement chamber with the actual sensor element, have highly tempered sensor regions due to heating of the sensor element to above 300° C.

It is important to thermally decouple the various components of the gas sensor, in particular the housing components and the sensor element and at the same time to simplify the complex structure and assembly of the known gas sensors.

This object is solved according to the invention by the features of claim 1. Further developments and advantageous embodiments of the solution according to the invention are obtained from the subclaims 2 to 9.

The gas sensor, in particular for automobile applications, comprising a housing, which has a measurement chamber, which is assigned at least one sensor element having connecting wires is characterised in that the housing has a bottom part and a top part that covers the bottom part and that each sensor element is arranged in the bottom part while suspended by the connecting wires, that the bottom part has an assembly opening in at least one of its side walls and that the top part is placed or arranged above the bottom part so that it can be joined or in the assembled state in such a manner that the side wall of the top part closes the assembly opening in the side wall of the bottom part.

It is a particular advantage of the solution according to the invention that the components of the gas sensor are restricted to a bottom part, a top part covering the bottom part and to at least one sensor element.

The bottom part encloses the actual measurement chamber which after attachment of the covering top part is present as a closed chamber. This prevents the heating on the chip comprising the sensor element from disadvantageously influencing other sensors and electronic parts in the surroundings.

This is in particular ensured by each sensor element and therefore each chip being arranged in the bottom part suspended on the connecting wires. The connecting wires are advantageously platinum coated wires on which the chip is suspended freely in the closed housing with the result that the heating is restricted to the chip or the sensor element.

The bottom part has a base and side walls emanating therefrom whose free ends correspond to the upper opening edge of the bottom part of the housing. The sensor element suspended on its connecting wires is located in the plane described by the upper opening edge of the bottom part.

At least one connecting surface is disposed on at least two mutually opposite side walls of the bottom part of the housing which each have a connecting region guided out from the housing.

The free ends of the connecting wires of the sensor element are guided to the opening edge of the bottom part of the housing and anchored there, for example, connected to the connecting surfaces provided there, which are disposed on at least two mutually opposite side walls of the bottom part.

Each connecting surface has respectively one connecting region guided out from the housing via which the sensor elements suspended on their connecting wires can communicate with a vehicle electronics system located outside. The connecting wires and the connecting surfaces are connected to one another, in particular by means of a weld connection, in particular by gas welding. We also talk here of bonding or wire bonding.

The gas sensor according to the invention is particularly advantageously characterised in that the assembly opening is formed in one of the side walls of the bottom part in such a manner that a tool arm holding the sensor element can be inserted through the assembly opening from outside into the bottom part as far as into the measurement chamber and can be brought into an assembly position in the area of the opening edge of the bottom part in such a manner that the connecting wires of the sensor element are in bondable contact with the associated solder connecting surfaces.

As a result, the manufacture of the gas sensor according to the invention is relatively simple and uncomplicated, which also results in cost advantages. The top part also has a cover part and side wall parts from which an external housing with lower opening edge is formed. An inner housing with upper opening edge is formed from the bottom part. According to the invention, the top part can be joined by means of the bottom part in such a manner that the side wall of the top part closes the assembly opening in the side wall of the bottom part. Thus, measures for closing the assembly openings of the gas sensor as soon as its sensor element is fastened in the bottom part forming an inner housing are superfluous.

The dimensions of the bottom part and the top part of the housing positioned thereover are selected so that between the bottom part forming the inner housing and the pulled-over top part forming the outer housing, there remains an air gap which brings about an advantageous insulation.

Furthermore, in the gas sensor according to the invention it is provided that the cover part of the top part has an opening in which a gas-permeable but liquid-impermeable closure element is disposed. The measurement chamber is thereby shielded against external influences. Advantageously the closure element is a membrane which is impermeable to water but open to vapour diffusion e.g. made of expanded PTFE (ePTFE). Other closure elements which have a shielding effect towards liquid water can also be used.

An exemplary embodiment of the invention from which further inventive features result is shown in the drawing.

The drawing shows a side view of a gas sensor according to the invention in section.

The gas sensor has a housing 1 which encloses a measurement chamber 2 and shields towards the outside. The housing 1 has a bottom part 3 and a top part 4 covering the bottom part. The bottom part 3 of the housing consists of a base 5 and side walls 6 and 7 going up from this. The free ends of the side walls form the upper opening edge 7 of the bottom part 3 of the housing 1. Located on at least two mutually opposite side walls 6, 7 of the bottom part 3 of the housing 1 is at least one connecting surface 8 or 8' which each have a connecting region 9, 9' guided out from the housing 1.

The bottom part 3 has an assembly opening 10 in its side wall 6 which is configured in such a manner that a tool arm 12 holding a sensor 11 can extend into the bottom part 3 and therefore into the measurement chamber 2. Thus, the sensor element can be brought into an assembly position in the region or in the plane of the opening edge 7 of the bottom part in such a manner that the connecting wires 13, 13' of the sensor element 11 are in bondable contact with the associated connecting surfaces 8, 8'.

After bonding the connecting wires 13, 13' to the connecting surfaces of the side walls 6, 7 of the bottom part 3, the tool arm 12 can be withdrawn outwards through the assembly opening with the sensor element now suspended on its connecting wires now remaining in the bottom part of the housing.

The top part 4 of the housing 1 is then lowered until it is located in the position shown by dashed lines. The assembly opening 10 in the side wall 6 of the bottom part 3 of the housing 1 is then closed.

The top part 4 consists of a cover part and side wall parts 15, 16. Cover parts and side wall parts form an outer housing with lower opening edge 17.

The cover part 14 of the top part 4 has an opening 18 in which a gas-permeable but liquid impermeable closure element is disposed. The closure element can, for example, be a membrane which is impermeable to liquid but open to vapour diffusion 19.

The invention claimed is:

1. A gas sensor, in particular for automobile applications, comprising:
   - a housing, which has a measurement chamber, which is assigned at least one sensor element having connecting wires,
   - wherein the housing has a bottom part and a separate top part,
   - wherein the bottom part has a base and side walls emanating therefrom, whose free ends correspond to an upper opening edge of the bottom part of the housing and has an assembly opening in at least one of its side walls and an assembly position for the sensor element in a region of the opening edge,
   - wherein the assembly opening is configured in such a manner that a tool arm holding the sensor element is introduced through the assembly opening from outside into the bottom part and is brought into an assembly position in a region of the opening edge of the bottom part in such a manner that the connecting wires of the sensor element are in bondable contact with associated solder connecting surfaces,
   - wherein the sensor element is suspended freely arranged by its connecting wires in the bottom part, the ends of the connecting wires being connected to the solder connecting surfaces, which are located on at least two mutually opposite side walls of the bottom part,
   - wherein the top part comprises a cover part and side wall parts from which an external housing is formed with a lower opening edge, and
   - the top part of the housing being arranged on the bottom part of the housing after the assembly of the sensor element in such a manner that the side walls of the top part closes the assembly opening in the side wall of the bottom part forming a closed measuring chamber.

2. The gas sensor according to claim 1, wherein at least one connecting surface is disposed on at least two mutually opposite side walls of the bottom part of the housing which each have a connecting region guided out from the housing.

3. The gas sensor according to claim 1, wherein an air gap is formed between bottom part and top part joined thereover.

4. The gas sensor according to claim 1, wherein the cover part of the top part has an opening in which a gas-permeable but liquid-impermeable closure element is disposed.

5. The gas sensor according to claim 4, wherein the closure element is a membrane.

\* \* \* \* \*